(12) United States Patent
Xiao et al.

(10) Patent No.: US 11,957,743 B2
(45) Date of Patent: Apr. 16, 2024

(54) STREPTOCOCCUS SUIS (S. SUIS) VACCINE

(71) Applicant: JIANGSU ACADEMY OF AGRICULTURAL SCIENCES, Nanjing (CN)

(72) Inventors: Qi Xiao, Nanjing (CN); Xialing Zhao, Nanjing (CN); Hongjie Fan, Nanjing (CN); Xiaoguo Huang, Nanjing (CN); Wenxian Qian, Nanjing (CN); Libin Wen, Nanjing (CN); Haodan Zhu, Nanjing (CN); Yanxiu Ni, Nanjing (CN); Junming Zhou, Nanjing (CN); Dandan Wang, Nanjing (CN); Jiaqiang Niu, Nanjing (CN); Kongwang He, Nanjing (CN)

(73) Assignee: JIANGSU ACADEMY OF AGRICULTURAL SCIENCES, Nanjing (CN)

( * ) Notice: Subject to any disclaimer, the term of this patent is extended or adjusted under 35 U.S.C. 154(b) by 0 days.

(21) Appl. No.: 18/272,371

(22) PCT Filed: Jun. 10, 2022

(86) PCT No.: PCT/CN2022/098076
§ 371 (c)(1),
(2) Date: Jul. 14, 2023

(87) PCT Pub. No.: WO2023/273829
PCT Pub. Date: Jan. 5, 2023

(65) Prior Publication Data
US 2024/0033339 A1 Feb. 1, 2024

(30) Foreign Application Priority Data
Jul. 2, 2021 (CN) .......................... 202110752883.1

(51) Int. Cl.
*A61K 39/09* (2006.01)
*A61K 39/39* (2006.01)
*A61P 31/04* (2006.01)
*A61K 39/00* (2006.01)

(52) U.S. Cl.
CPC ............ *A61K 39/092* (2013.01); *A61K 39/39* (2013.01); *A61P 31/04* (2018.01); *A61K 2039/552* (2013.01); *A61K 2039/55511* (2013.01); *A61K 2039/55566* (2013.01)

(58) Field of Classification Search
None
See application file for complete search history.

(56) References Cited

U.S. PATENT DOCUMENTS

2019/0336594 A1  11/2019  Jacobs
2021/0015910 A1   1/2021  Seele et al.

FOREIGN PATENT DOCUMENTS

| CN | 101613399 A | 12/2009 |
| CN | 104248754 A | 12/2014 |
| CN | 108671227 A | 10/2018 |
| CN | 109180822 A | 1/2019 |
| CN | 112063561 A | 12/2020 |
| CN | 112409495 A | 2/2021 |
| CN | 112410310 A | 2/2021 |
| CN | 113332421 A | 9/2021 |
| WO | 2018162428 A1 | 9/2018 |

OTHER PUBLICATIONS

Ye et al. The Journal of Infectious Diseases. 2009; 199:97-107.*
Uniprot Accession D5AI23 Jun. 15, 2020.*
Quan Li, et al., Live attenuated *Salmonella enterica* serovar Choleraesuis vector delivering a conserved surface protein enolase induces high and broad protection against *Streptococcus suis* serotypes 2, 7, and 9 in mice, Vaccine, 2020, pp. 6904-6913, vol. 38.
Minu Shinoy, et al., Immunoproteomic Analysis of Proteins Expressed by Two Related Pathogens, *Burkholderia multivorans* and *Burkholderia cenocepacia*, during Human Infection, PLoS ONE, 2013, pp. 1-15, vol. 8 Issue 11, e80796.
Esther Prados De La Torre, et al., Proteomic and Bioinformatic Analysis of *Streptococcus suis* Human Isolates: Combined Prediction of Potential Vaccine Candidates, Vaccines, 2020, pp. 1-22, vol. 8 No. 188.
Chen Chen, et al., A Glimpse of Streptococcal Toxic Shock Syndrome from Comparative Genomics of S. suis 2 Chinese Isolates, PLoS ONE, 2007, pp. 1-9, vol. 2 Issue 3, e315.
GenBank: ABP90138.1, F0F1-type ATP synthase, beta subunit [*Streptococcus suis* 05ZYH33], 2014.

* cited by examiner

*Primary Examiner* — Oluwatosin A Ogunbiyi
(74) *Attorney, Agent, or Firm* — Bayramoglu Law Offices LLC

(57) ABSTRACT

A *Streptococcus suis* (S. suis) vaccine is provided. For the S. suis vaccine, an antigen is a protein with an amino acid sequence shown in SEQ ID NO: 2. A preparation method of the S. suis vaccine is provided, including the following steps: mixing a white oil and aluminum stearate to obtain a white oil adjuvant; adding poly sorbate 80 to an aqueous solution of the protein with the amino acid sequence shown in SEQ ID NO: 2, and thoroughly mixing to obtain an antigen solution; and mixing the antigen solution with the white oil adjuvant according to a volume ratio of (0.5-1.5):2, and emulsifying to obtain the S. suis vaccine. An animal immunized with the S. suis vaccine of the present disclosure can effectively resist the attack of S. suis serotype 2, 3, and 31, with a vaccine protection rate as high as 100%.

7 Claims, 5 Drawing Sheets

Specification includes a Sequence Listing.

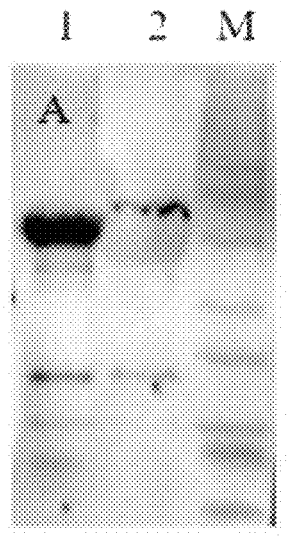 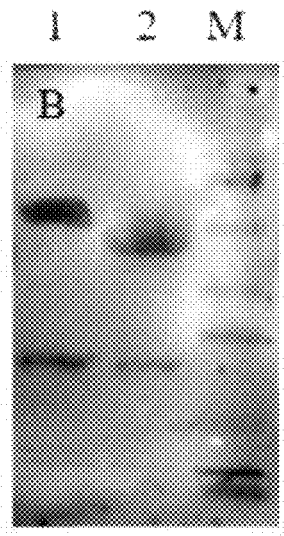 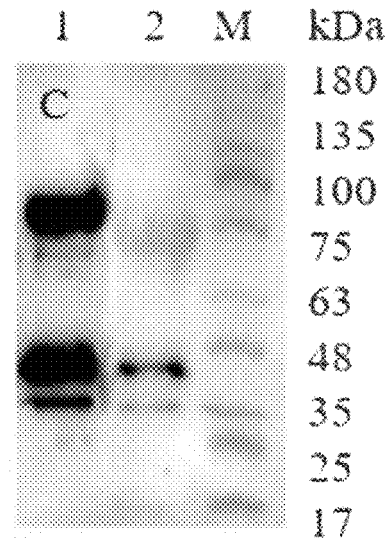
FIG. 5A          FIG. 5B          FIG. 5C
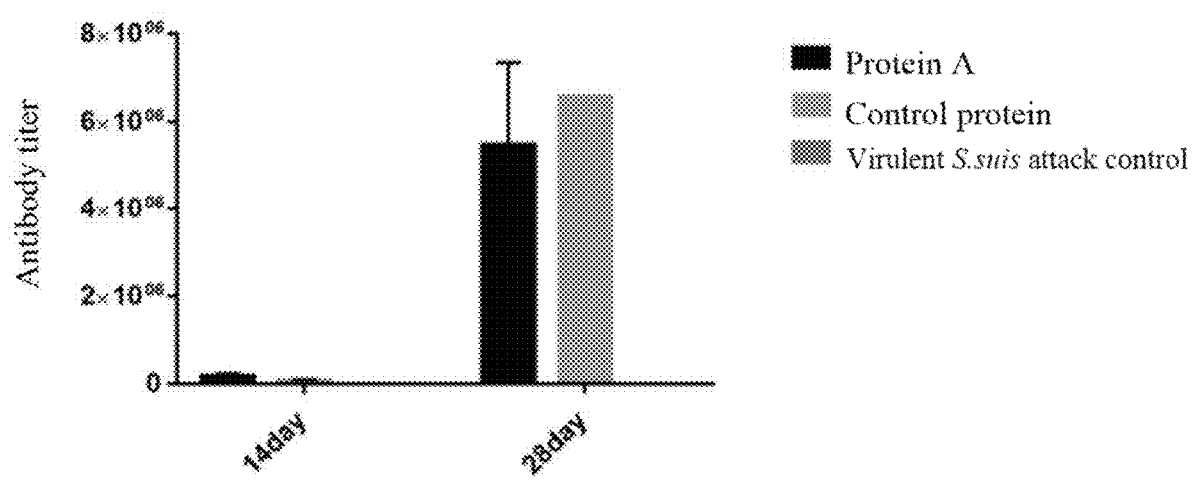
FIG. 6

TNF-α

STREPTOCOCCUS SUIS (S. SUIS) VACCINE

CROSS REFERENCE TO THE RELATED APPLICATIONS

This application is the national phase entry of International Application No. PCT/CN2022/098076, filed on Jun. 10, 2022, which is based upon and claims priority to Chinese Patent Application No. 202110752883.1, filed on Jul. 2, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBHS011-PKG_Sequence_Listing.txt, created on Apr. 14, 2023, and is 14,001 bytes in size.

TECHNICAL FIELD

The present disclosure relates to the field of veterinary vaccines, and specifically to a Streptococcus suis (S. suis) vaccine.

BACKGROUND

S. suis is an important zoonotic pathogen that causes serious food safety problems, and years of antibiotic abuse has led to the emergence of drug resistance, which poses a challenge to the prevention and treatment of S. suis infection. However, researchers have immunized an animal with a whole-cell bacterial vaccine for S. suis, and immunization results show that the whole-cell inactivated vaccine can only provide a limited immunoprotection effect for S. suis of different serotypes.

In the prior art, there is a lack of a vaccine that can resist the attack of S. suis serotype 3 and 31, let alone a vaccine that can resist the attack of each of S. suis serotype 2, 3, and 31.

SUMMARY

An Objective of the present disclosure is to provide an S. suis vaccine that can resist the attack of each of S. suis serotypes 2, 3, and 31.

The objective of the present disclosure is achieved through the following technical solutions:

A S. suis vaccine is provided, where an antigen is a protein with an amino acid sequence shown in SEQ ID NO: 2.

In the present disclosure, an adjuvant in the S. suis vaccine is a white oil.

The present disclosure also provides a preparation method of the S. suis vaccine, including the following steps: mixing a white oil and aluminum stearate to obtain a white oil adjuvant; adding Tween-80 to an aqueous solution of the protein with the amino add sequence shown in SEQ ID NO: 2, and thoroughly mixing to obtain an antigen solution; and mixing the antigen solution with the white oil adjuvant according to a volume ratio of (0.5-1.5):2, and emulsifying to obtain the S. suis vaccine.

In the present disclosure, the protein is obtained by inserting a coding gene for the protein into a vector, introducing the vector into a host strain, and inducing expression.

In the present disclosure, the coding gene for the protein has a sequence shown in SEQ ID NO: 1.

In the present disclosure, a mass ratio of the white oil to the aluminum stearate is (90-120):2.5.

In the present disclosure, the aqueous solution of the protein has a concentration of 0.9 mg/mL to 1.2 mg/mL.

In the present disclosure, a volume of the Tween-SO is 2% to 6% of a volume of the aqueous solution of the protein.

The present disclosure has the following beneficial effects: An animal immunized with the S. suis vaccine of the present disclosure exhibits a protection rate as high as 100% against the attack of S. suis serotype 2, 3, and 31. As a versatile S. suis vaccine, the S. suis vaccine of the present disclosure can significantly reduce the production cost and vaccination workload, and can also reduce the stress response of an immunized animal.

BRIEF DESCRIPTION OF THE DRAWINGS

FIGS. 5A-5C show Western Blot (WB) results of a protein A and a control protein, where a primary antibody in FIG. 5A is hyperimmune serum from a mouse immunized against S. suis serotype 2, a primary antibody in FIG. 5B is hyperimmune serum from a mouse immunized against S. suis serotype 3, and a primary antibody in FIG. 5C is hyperimmune serum from a mouse immunized against S. suis serotype 31; and lane 1 is for the protein A, lane 2 is for the control protein, and M is for a protein molecular weight marker (KDa).

FIG. 6 shows the serum antibody titer of mice, where the abscissa represents a number of days after the primary immunization and the ordinate represents an antibody titer; and the protein A and the control protein refer to a protein A vaccine-immunized group and a control protein vaccine-immunized group, respectively, and the virulent S. suis attack control refers to a virulent S. suis attack control group.

FIG. 9 shows the relative expression of TNF-α in spleens of mice in each group, where the protein A and the control protein refer to a protein A vaccine-immunized group and a control protein vaccine-immunized group, respectively, and the attack group refers to a virulent *S. suis* attack control group; and * indicates P<0.05 compared with the virulent *S. suis* attack control group and ns indicates P>0.05 compared with the virulent *S. suis* attack control group, without a significant difference.

DETAILED DESCRIPTION OF THE EMBODIMENTS

1. Experimental Animals

Figure 1:
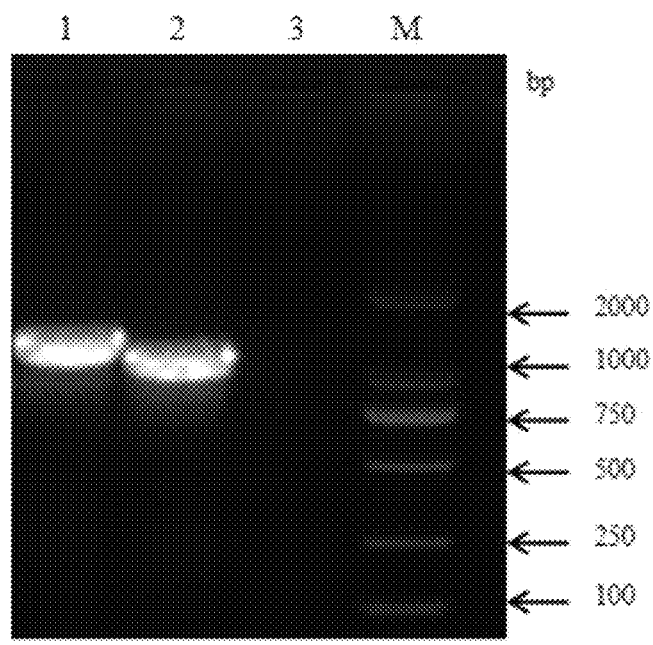
FIG. 1 is an electrophoregram of polymerase chain reaction (PCR) amplification products of a protein A-coding gene and a control protein-coding gene, where Lane 1 to Lane 3 are for a PCR amplification product of the protein A-coding gene, a PCR amplification product of the control protein-coding gene, and a negative control, respectively; and M is for DL2000 DNA Marker.

BALB/c female mice purchased from the Shanghai Lab Annual Research Center.

2. Main Reagents

Gel Extraction Kit and Plasmid Mini Kit I purchased from Omega; restriction endonucleases and T4 DNA ligase purchased from Takara Bio; isopropyl-β-D-thiogalactoside (IPTG) purchased from Sangon Biotech (Shanghai) Co., Ltd.; total RNA mini kit purchased from Guangzhou Magen Biotechnology Co., Ltd.; Ni-TED agarose purification resin purchased from BBI Life Sciences Corporation; and Hi Script II Q RT SuperMix for qPCR purchased from Nanjing Vazyme Biotech Co., Ltd.

3. Main Instruments

Spectrophotometer (model: Evolution 200) from Thermo Fisher Scientific; refrigerated thermostatic oscillator (model: THZ-C-L) from Taicang Johnson & Johnson Experimental Equipment Co., Ltd.; constant-temperature incubator (model: DNP-9272) from Shanghai Precision Experimental Equipment Co., Ltd.; PCR instrument (model: Mastercy-Cler® nexus) from eppendoef; electrophoresis instrument (model: DYY-11) from Beijing Liuyi instrument Factory; automatic digital gel imaging instrument (model: Fallon 3500) and chemiluminescence instrument (model: Tanon 5200) from TIANGEN Biotech Co., Ltd.; ultrasonic cell disruptor (model: XO-1000D) from Nanjing Xianou Instruments Manufacture Co., Ltd.; semi-dry transfer cell (model: Trans-Blot SD 1703940) from Bio-Rad; and automatic microplate reader (model: ELx800) from BIO-TEK.

4. Reagent Preparation

Preparation of 100 mg/mL ampicillinum: 100 mg of an ampicillin antibiotic powder is dissolved in 1 mL of distilled water, and a resulting solution is filtered through a 0.22 μL filter and then stored at −20° C.

Binding buffer: 240 g of urea is added to 500 mL of 20 Mm phosphate buffered saline (PBS) at pH 7.4, and a resulting mixture is stirred for dissolution.

Coating solution: 1.59 g of $Na_2CO_3$, 2.93 g of $NaHCO_3$, and 0.2 g of $NaN_3$ are dissolved in water, and a resulting solution is diluted to 1,000 mL with water, sealed, and stored at 4° C.

Washing solution (PBST): 8 g of NaCl, 0.2. g of KCl, 3.58 g of $Na_2HPO_4.12H_2O$, 0.27 g of $KH_2PO_4$, and 0.5 mL of Tween-20 (polysorbate 20) are dissolved in water, and a resulting solution is diluted to 1,000 mL with water.

Blocking solution: Skimmed milk powder (SMP) is added at a final concentration of 5% (mass percentage concentration) to the washing solution (PBST), and a resulting mixture is thoroughly mixed.

Stop solution: A 2 M $H_2SO_4$ aqueous solution is prepared.

EXAMPLE 1

Construction of a Recombinant Strain for Preparing a Vaccine Antigen

In order to find an effective antigen for a universal *S. suis* vaccine, a large number of antigens were screened by an immunoproteomics method, and it was finally found that a vaccine prepared with a protein A as an immunogen could resist the attack of *S. suis* serotype 2, 3, and 31. The protein A had a gene sequence shown in SEQ ID NO: 1 and an amino acid sequence shown in SEQ ID NO: 2.

1. PCR primers

Primers A-P1 and A-P2 were designed to amplify a coding gene for the protein A. In addition, primers B-P1 and B-P2 were designed to amplify a coding gene for a control protein. The control protein had a gene sequence shown in SEQ ID NO: 3 and an amino acid sequence shown in SEQ ID NO: 4. Specific sequences of the primers were shown in Table 1, and the primers were synthesized by Nanjing GenScript Biotech Co., Ltd.

TABLE 1

Primer sequences

| Target sequence | Primer sequence (5'→3') | Fragment size/bp | Annealin temperature (° C.) | Enzymatic cleavage site |
|---|---|---|---|---|
| Protein A-coding gene | A-P1: P1: CCGAATTCATGAGTTCAGGCAAAATTACTCAGG (SEQ ID NO: 5) | 1407 | 63 | EcoRV |
| | A-P2: CCGCTCGAGGAATTTCATTTTAGCAGCTTTAGCG (SEQ ID NO: 6) | | | XhoI |
| Control protein-coding gene | B-P1: CCGAATTCATGACAAAATTAAATCGTGTAGTAG (SEQ ID NO: 7) | 1236 | 60 | EcoRV |
| | B-P2: CCGCTCGAGGGCCTCCCAACGTTTGAAAGCG (SEQ ID NO: 8) | | | XhoI |

Note:
A marked horizontal line in Table 1 indicates an enzymatic cleavage site.

2. Extraction of DNA from *S. suis*

DNA was extracted from *S. suis* according to a conventional method.

3. PCR Amplification of Coding Genes for the Protein A and Control Protein

With DNA of *S. suis* serotype 3 JSHZ (published in the patent application No. 202011000342.5) as a template, primers of each target protein were used to amplify the protein A-coding gene and the control protein-coding gene through PCR, respectively. A PCR system was shown in Table 2.

TABLE 2

PCR system for the target gene

| Reactant name | Volume |
| --- | --- |
| Green Tap Mix | 25 µL |
| Upstream primer | 2 µL |
| Downstream primer | 2 µL |
| *S. suis* DNA | 1 µg |
| dd H$_2$O | Making up to 50 µL |

A PCR amplification procedure was as follows: 95° C. for 3 min; 95° C. for 15 s; annealing temperature (protein A annealing temperature: 63° C., and control protein annealing temperature: for 15 s, and 72° C. for 90 s, with 35 cycles; and 72° C. for 5 min.

After a PCR procedure was completed, 8 µL of a PCR amplification product was taken and identified by 1% agarose gel electrophoresis.

The agarose gel electrophoresis identification results of PCR amplification products of the protein A-coding gene and the control protein-coding gene were shown in FIG. 1. It can be seen from FIG. 1 that a specific target band appears at 1,407 bp for an amplification product of the protein A-coding gene, and a specific target band appears at 1,236 bp for an amplification product of the control protein-coding gene, each of which is of an expected size.

5. Recovery of Target Fragments

A GeL Extraction Kit from Omega was used to recover PCR amplification products for the protein A-coding gene and control protein-coding gene, respectively.

6. Digestion and Ligation of a Target Gene and a pET-32a(+) Vector

The recovered PCR amplification product for the protein A-coding gene and a pET-32a(+) vector each were subjected to double enzyme digestion with restriction endonucleases EcoRV and XhoI (an enzyme digestion system was shown in Table 3) at 37° C. for 1 h, a digestion product was taken and subjected to agarose electrophoresis, and a target fragment was recovered with a gel recovery kit. According to the ligation system in Table 4, T4 DNA Ligase and 10×T4 DNA Ligase Butler were added to DNA obtained after the double enzyme digestion and gel recovery of the protein A-coding gene and DNA obtained after the double enzyme digestion and gel recovery of the vector, and a resulting mixture was subjected to ligation at 16° C. for 2 h to obtain a recombinant plasmid 1 carrying the protein A-coding gene. In addition, a control recombinant plasmid carrying the control protein-coding gene was constructed according to the construction method of the recombinant plasmid 1 carrying the protein A-coding gene.

TABLE 3

Enzyme digestion system

| Reagent | Volume |
| --- | --- |
| Restriction endonuclease EcoRV | 1 µL |
| Restriction endonuclease XhoI | 1 µL |
| 10 × Fast Green Buffer digestion buffer | 2 µL |
| PCR amplification product of protein A or control protein-coding gene/vector | 1 µg |
| dd H$_2$O | Making up to 20 µL |

TABLE 4

Ligation system

| Reagent | Volume |
| --- | --- |
| DNA obtained after the double enzyme digestion and gel recovery of a protein-coding gene | 0.3 pmoL |
| DNA obtained after the double enzyme digestion and gel recovery of the vector | 0.03 pmoL |
| T4 DNA Ligase | 1 µL |
| 10 × T4 DNA Ligase Buffer | 2.5 µL |

7. Transformation of a Ligation Product into a Trans 5α Chemical Competent Cell

The recombinant plasmid 1 and the control recombinant plasmid each were transformed into the Trans 5α chemical competent cell (purchased from TransGen Biotech Co., Ltd.), and specific steps were as follows:

(1) The Trans 5α chemical competent cell was taken and thawed in ice.

(2) 2 µL of the recombinant plasmid was added to 50 µL of the Trans 5α chemical competent cell in an EP tube, a bottom of the EP tube was gently flicked with hands, and then the EP tube was allowed to stand in ice for 30 min, subjected to heat shock at 42° C. for 45 s, and immediately allowed to stand on ice for 2 min, and 700 µL of a non-resistant liquid LB medium was added, and the EP tube was incubated at 37° C. and 200 r/min under shaking for 1 h.

(3) The EP tube was centrifuged at 5,000 r/min for 3 min, 400 µL, of a resulting supernatant was discarded, and the EP tube was vortexed, and 100 µL of a resulting suspension was uniformly coated on an ampicillin-resistant LB solid medium and cultivated overnight at 37° C.

8. Identification of Positive Clones

Single colonies were picked from the LB solid medium obtained in section 7, inoculated into mL, of an ampicillin-resistant LB liquid medium, and cultivated at 37° C. and 200 r/min under shaking for 12 h to 16 h, and 1 µL of a resulting bacterial solution was taken for bacterial liquid PCR verification. A positive clone that had been successfully transformed with the recombinant plasmid 1 was named a recombinant strain 1. A positive clone that had been successfully transformed with the control recombinant plasmid was named a control recombinant strain 1.

9. Extraction of Plasmids

The recombinant plasmids in the recombinant strain 1 and the control recombinant strain 1 each were extracted with Plasmid Mini Kit I of Omega.

10. Digestion Identification of Recombinant Plasmids

Figure 2:
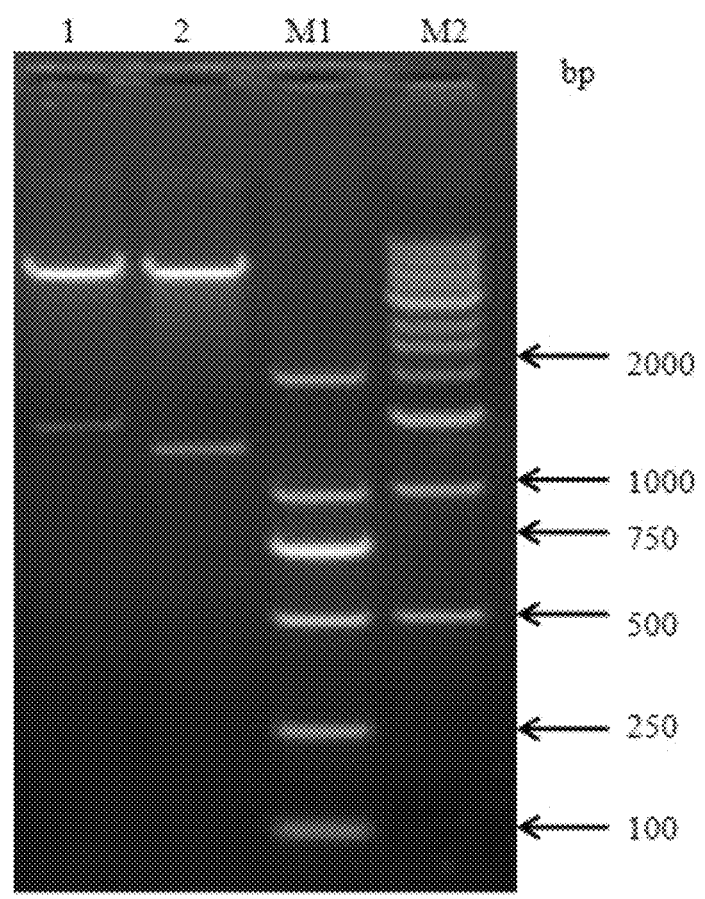
FIG. 2 is an electrophoregram for digestion identification of recombinant plasmids, where Lane 1 and Lane 2 are for digestion products of a recombinant plasmid 1 and a control recombinant plasmid, respectively; M1 is for DL2000 DNA Marker; and M2 is for DL5000 DNA Marker.

The extracted recombinant plasmid 1 and control recombinant plasmid each were subjected to double enzyme digestion with restriction endonucleases EcoRV and XhoI, and after the digestion was completed, identification was conducted by agarose electrophoresis. Results were shown in FIG. 2. A digestion product of the recombinant plasmid 1 had specific bands at 1,407 bp and 5,886 bp, and a digestion product of the control recombinant plasmid had specific bands at 1,236 bp and 5,886 bp, indicating that a corresponding target band was amplified for each of the exogenous gene and the pET-32a(+) vector. In addition, the correct insertion of the target gene was confirmed through genome sequencing.

11. Transformation of a Ligation Product into a Trans BL21(DE3)pLysS Chemical Competent Cell The recombinant plasmid 1 and the control recombinant plasmid each were transformed into the Trans BL21(DE3) pLysS chemical competent cell (purchased from TransGen Biotech Co., Ltd.), and a specific method was as follows:

(1) The Trans BL21(DE3)pLysS chemical competent cell was taken and thawed in ice.

(2) 2 μL of the recombinant plasmid was added to 50 μL of the Trans BL21(DE3)pLysS chemical competent cell in an EP tube, a bottom of the EP tube was gently flicked with hands, and then the EP tube was allowed to stand in ice for 30 min, subjected to heat shock at 42° C. for 45 s, and immediately allowed to stand on ice for 2 min; and 700 μL of a non-resistant liquid LB medium was added, and the EP tube was incubated at 37° C. and 200 r/min under shaking for 1 h.

(3) A bacterial solution obtained after the cultivation was centrifuged at 5,000 r/min for 3 min, 400 μL of a resulting supernatant was discarded, and the EP tube was vortexed; and 100 μL of a resulting suspension was uniformly coated on an ampicillin-resistant LB solid medium and cultivated overnight at 37° C.

(4) Single colonies were picked, inoculated into 5 mL of an ampicillin-resistant LB liquid medium, and cultivated at 37° C. and 200 r/min under shaking for 12 h to 16 h, and 1 μL of a resulting bacterial solution was taken for bacterial liquid PCR verification. Trans BL21 (DE3)pLysS that had been successfully transformed with the recombinant plasmid 1 was named a recombinant strain 2. Trans BL2I(DE3)pLysS that had been successfully transformed with the control recombinant plasmid was named a control recombinant strain 2.

In addition, with reference to the same method as above, the pET-32a(+) vector was transformed into Trans BL21 (DE3)pLysS to obtain a control recombinant strain 3.

II Protein Expression and Purification

1. Induced Expression

The recombinant strain 2, the control recombinant strain 2, and the control recombinant strain 3 each were subjected to induced expression. A specific method was as follows: A seed culture of the recombinant strain was added to an LB liquid medium with 100 mg/mL ampicillinum according to a volume ratio of 1:100, the strain was cultivated at 37° C. and 150 r/min until a resulting bacterial solution had an OD value of 0.4 to 0.6, then IPTG was added at a final concentration of 0.8 mmoL/L, and then induced expression was conducted in a shaking incubator at 16° C. and 150 r/min for 16 h; after the induced expression was completed, 4 mL of a resulting bacterial solution was taken and centrifuged at 12,000 r/min for 3 min, a resulting supernatant was discarded, resulting bacterial cells were washed with PBS 2 to 3 times, and 500 μL of PBS was added to resuspend the bacterial cells; a resulting bacterial suspension was subjected to ultrasonic disruption on ice until a clear solution was obtained, and after the ultrasonic disruption was completed, a resulting solution was centritliged at 12,000 r/min for 10 min; and a lysate supernatant and a lysate precipitate were collected separately, and the lysate precipitate was resuspended with Binding buffer to obtain a lysate precipitate suspension.

2. SDS-PAGE

Figure 3:
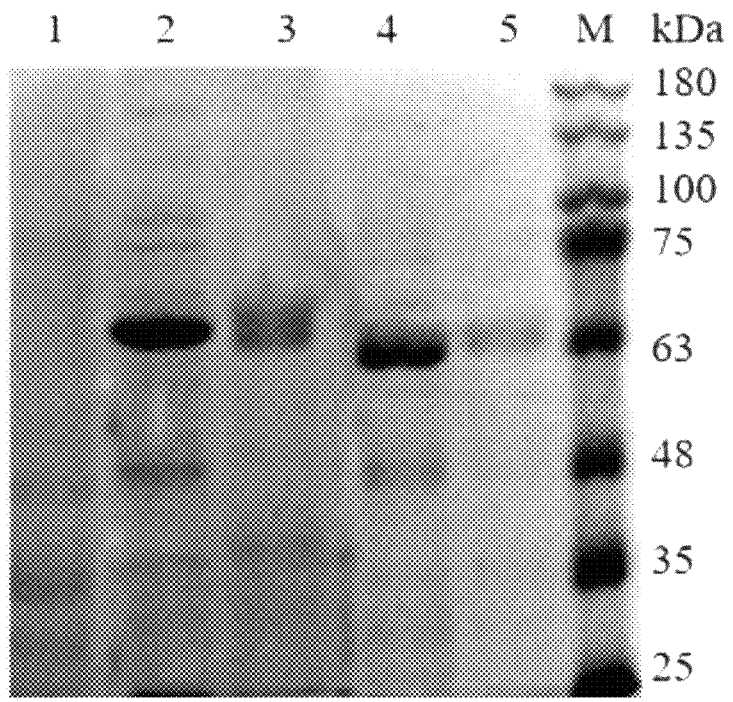
FIG. 3 shows sodium dodecyl sulfate-polyacrylamide gel electrophoresis (SDS-PAGE) results for induced expression of a protein A and a control protein, where Lane 1 to Lane 5 are for a control recombinant strain 3 (introduced with an empty vector pET-32a(+)), a lysate supernatant of a recombinant strain 2. a lysate precipitate suspension of the recombinant strain 2, a lysate supernatant of a control recombinant strain 2, and a lysate precipitate suspension of the control recombinant strain 2, respectively; and M is for a protein molecular weight marker (KDa).

48 μL of each of a lysate supernatant and a lysate precipitate suspension obtained after the induced expression of each strain in the previous step was taken and added to a new EP tube, then 12 μL of 5×SDS gel loading buffer was added, a resulting mixture was heated at 100° C. for 10 min, and 10 μL of a resulting reaction system was taken and subjected to SDS-PAGE. Results were shown in FIG. 3. The protein A had a specific band at 70 KDa and the control protein had a specific band at 62 KDa; and both the protein A and the control protein were mainly expressed in the supernatant with a high expression level, that is, the two mainly underwent soluble expression.

3. Purification and WB of Proteins

The recombinant strain 2, the control recombinant strain 2, and the control recombinant strain 3 each were subjected to induced expression in accordance with the method in section 1 of part II (Protein expression and purification) in this example, and a lysate supernatant of each recombinant strain was collected, filtered through a 0.45 μm filter, and then purified by a Ni-TED agarose purification resin column of BBI Life Sciences Corporation to obtain a protein A, a control protein, and a protein expressed by the control recombinant strain 3. A specific purification method could be seen in instructions of the Ni-TED agarose purification resin column.

Figure 4:
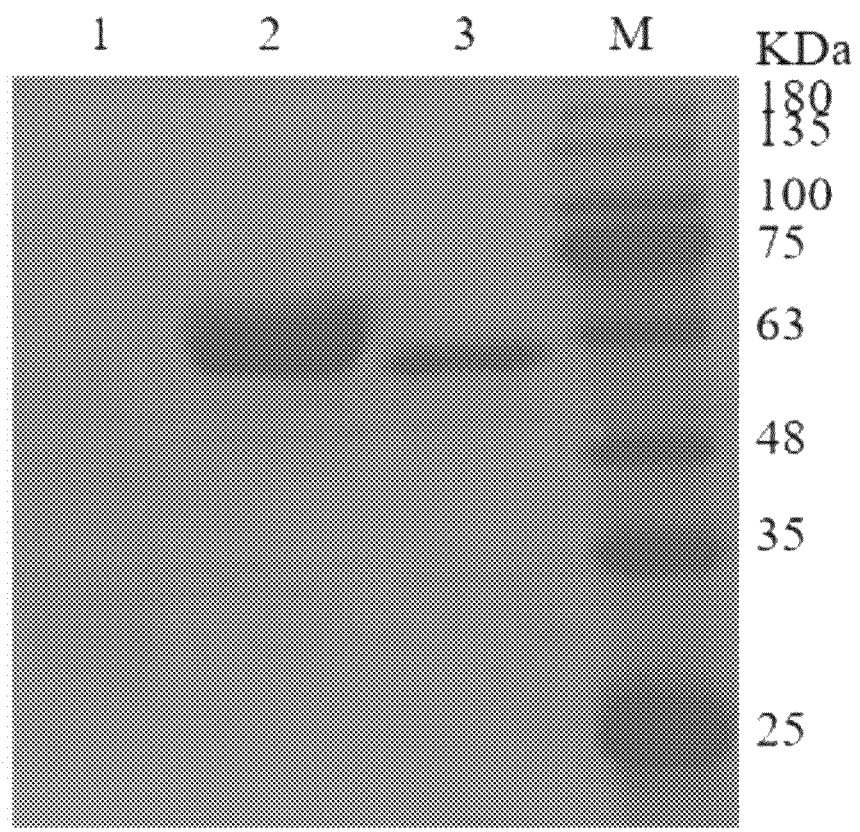
FIG. 4 shows SDS-PAGE results of a purified protein A and a control protein, where Lane 1 to Lane 3 are for a purified protein expressed by a control recombinant strain 3, a protein A, and a control protein; and M is for a protein molecular weight marker (KDa).

The purified protein A, control protein, and protein expressed by the control recombinant strain 3 each were detected by SDS-PAGE. Results were shown in FIG. 4. The protein A had a specific band at 70 KDa and the control protein had a specific band at 62 KDa, both of which had no impurity band and had a high purity.

Moreover, the purified protein A and control protein each were transferred to an nitrocellulose (NC) membrane (purchased from GE in the United States) after the SDS-PAGE, and 5% SMP-containing PBST was added to block at room temperature for 2 h; hyperimmune serum obtained from a mouse immunized against each of *S. suis* serotype 2, 3, and 31 was added as a primary antibody, and a resulting mixture was incubated for 2 h at room temperature; sheep anti-mouse IgG labeled with horseradish peroxidase (HRP) was added as a secondary antibody, and a resulting mixture was incubated at room temperature for 1 h; and finally chromogenic exposure was conducted under an action of an enhanced chemiluminescence (ECL) solution. Results were shown in FIGS. 5A-5C.

EXAMPLE 2

Immune Efficacy of Protein A

1. Active Immunization of Mice

The purified protein A was prepared into a vaccine as follows: 117.5 ml, of a white oil was mixed with 2.5 g of aluminum stearate, and a resulting mixture was vigorously shaken, autoclaved, cooled to about 50° C., and then vigorously shaken to obtain a white oil adjuvant in a transparent homogeneous state; an aqueous solution of the purified protein A in a concentration of 1.08 mg/mL was prepared, sterilized Tween-80 (polysorbate 80) was added in a volume 4% of a volume of the aqueous solution of the purified protein A, and a resulting mixture was thoroughly mixed to obtain an antigen solution; and the antigen solution was mixed with the white oil adjuvant according to a volume ratio of 1:2, and a resulting mixture was emulsified to obtain a protein A vaccine.

With the same method, a control protein was used instead of the protein A to prepare a corresponding vaccine, which was recorded as a control protein vaccine. An antigen concentration in the control protein vaccine was the same as an antigen concentration in the protein A vaccine.

A blank vaccine was prepared by the same method as the preparation method of the protein A vaccine, except that the same volume of PBS (concentration: 0.01 M, pH: 7.4) was used instead of the protein A.

4-week-old BALB/c female mice were randomly divided into 4 groups with 18 mice per group, including: 2 experimental groups (protein A vaccine-immunized group and control protein vaccine-immunized group), a blank vaccine control group, and a virulent *S. suis* attack control group. Each mouse in each experimental group was intraperitoneally injected with 200 μL of a corresponding vaccine that included 60 μg of an antigen protein; and each mouse in the control group was injected with 200 μL of the blank vaccine. 14 days after the primary immunization, mice in each group were subjected to secondary immunization by the same method as the primary immunization. Mice in the virulent *S. suis* attack control group were not immunized.

2. Immunoprotection of Mice from Virulent *S. suis* Attack

Mice in the protein A vaccine-immunized group, control protein vaccine-immunized group, and blank vaccine control group were subjected to virulent *S. suis* attack two weeks after the secondary immunization. Mice in each of the immunized groups and the control group were randomly divided into 3 groups with 5 mice per group, and the three groups were infected with *S. suis* serotype 2, 3, and 31, respectively; and mice in the virulent *S. suis* attack control group were randomly divided into 3 groups with 5 mice per group, and the 3 groups were infected with *S. suis* serotype 2, 3, and 31, respectively. After the mice were subjected to virulent *S. suis* attack, the mice were observed continuously for 7 d, during which the clinical symptoms and death of the mice were recorded. Results were shown in Table 5. After the virulent *S. suis* attack, the mice in the virulent *S. suis* attack control group showed obvious clinical symptoms such as mental malaise, messy coat, and gathering, where all of the mice attacked by *S. suis* serotype 2 and 3 died, and 4 of the mice attacked by *S. suis* 31 died. All of the mice attacked by *S. suis* serotype 2, 3, and 31 in the blank vaccine control group died. After the virulent *S. suis* attack, some of the mice in the experimental group showed symptoms such as messy coat, gathering, and mental malaise, but these symptoms disappeared within 48 h to 72 h. None of the mice in the protein A vaccine-immunized group that were attacked by *S. suis* serotype 2, 3, and 31 died, indicating a survival rate of 100%. None of the mice in the control protein vaccine-immunized group that were attacked by *S. suis* serotype 2 and 31 died, indicating a survival rate of 100%, but 2 of the mice in the control protein vaccine-immunized group that were attacked by *S. suis* serotype 3 died, indicating a survival rate of only 60%.

TABLE 5

Immunoprotection rate of each protein for mice

| Grouping | *S. suis* serotype 2 attack | *S. suis* serotype 3 attack | *S. suis* serotype 31 attack |
| --- | --- | --- | --- |
| Protein A vaccine-immunized group | 100% (5/5) | 100% (5/5) | 100% (5/5) |
| Control protein vaccine-immunized group | 100% (5/5) | 60% (3/5) | 100% (5/5) |
| Blank vaccine control group | 0 (0/5) | 0 (0/5) | 0 (0/5) |
| Virulent *S. suis* attack control group | 0 (0/5) | 0 (0/5) | 20% (1/5) |

Note:
The data in parentheses in Table 5 represent in the form of number of surviving mice/total number of attacked mice.

3. Enzyme-Linked Immunosorbent Assay (ELISA) Detection of Mouse Serum Antibody Titer On day 14 and day 28 after the primary immunization of mice, 3 mice were randomly selected. from each group, blood was collected from the orbit, and serum was isolated through centrifugation and stored at −20° C. The serum antibody titer was determined by indirect ELISA.

A detection method of the mouse serum antibody titer for the protein A was specifically as follows: The coating solution was used to prepare the protein A into a solution with a concentration of 0.3135 μg/mL, and an ELISA plate was coated with the solution at 100 μL/well, incubated overnight at 4° C., and washed with the washing solution 3 times for 3 min each time; then 150 μL of the blocking solution was added to each well to block at 37° C. for 30 min, and the ELISA plate was washed with the washing solution; serum to be tested from a mouse in the protein A vaccine-immunized group was diluted 2-fold (dilution ratio: 1:400 to 1:6553600), 100 μL of a serum dilution was added to each well, and the ELISA plate was incubated at 37° C. for 1 h and then washed with the washing solution 3 times; sheep anti-mouse IgG-HRP (purchased from Beijing TransGen Biotech Co., Ltd., Item No. HS201-01) was diluted by 1:4000, 100 μL of a resulting dilution was added to each well, and the ELISA plate was incubated at 37° C. for 1 h and then washed with the washing solution 3 times; 100 μL of a TMB chromogenic solution (purchased from Huzhou InnoReagents Co., Ltd., Item No. TMB-S-001) was added to each well, and a reaction was allowed for 15 min in the dark; and 50 μL of the stop solution was added to each well, and the $OD_{450}$ was determined on a microplate reader. The antibody titer was calculated by a conventional method.

A detection method of the mouse serum antibody titer for the control protein was specifically as follows: The coating solution was used to prepare the control protein into a solution with a concentration of 5 μg/mL, and an ELISA plate was coated with the solution at 100 μL/well, incubated overnight at 4° C., and washed with the washing solution 3 times for 3 min each time; then 150 μL of the blocking solution was added to each well to block at 37° C. for 30 min, and the ELISA plate was washed with the washing solution; serum to be tested from a mouse in the control protein vaccine-immunized group was diluted 2-fold (dilution ratio: 1:400 to 1:6553600), 100 μL of a serum dilution was added to each well, and the ELISA plate was incubated at 37° C. for 1 h and then washed with the washing solution 3 times; sheep anti-mouse IgG-HRP (purchased from Beijing TransGen Biotech Co., Ltd., Item No. HS201-01) labeled with HRP was diluted by 1:4000, 100 of a resulting dilution was added to each well, and the ELISA plate was incubated at 3 7 ° C. for 1 h and then washed with the washing solution 3 times; 100 μL, of a TMB chromogenic solution (purchased from Huzhou InnoReagents Co., Ltd. ; Item No. TMB-S-001) was added to each well, and a reaction was allowed for 15 min in the dark; and 50 μL of the stop solution was added to each well, and the $OD_{450}$ was determined on a microplate reader. The antibody titer was calculated by a conventional method.

Results were shown in FIG. 6. In the mice of the protein A vaccine-immunized group and the control protein vaccine-immunized group, a specific antibody could be detected with a high antibody level 14 days after the secondary immunization.

6. Detection of Expression Levels of Relevant Cytokines by Real-Time Quantitative Reverse Transcription-PCR (qRT-PCR)

(1) Extraction of RNA from the Spleen 14 days after the secondary immunization, 3 mice were randomly selected from each group, and RNA was extracted from the spleen of mice in each group with HiPure Total RNA Mini Kit of Magen.

(2) Reverse Transcription of RNA into cDNA

A HiScript II RT SuperMix for qPCR, (+gDNA wiper) reagent of Vazyme was used to reverse-transcribe each RNA in step (1) into cDNA. A specific method was as follows: According to Table 6, a mixed solution was prepared in an RNase-free centrifuge tube, gently pipetted up and down for thorough mixing, and placed at 42° C. for 2 min. Then, 4 μL of 5× HiScript II RT SuperMix for qPCR was added, a resulting mixture was gently pipetted up and down for thorough mixing, and then a reverse transcription reaction was conducted according to the procedure in Table 7 to obtain cDNA.

TABLE 6

Reverse transcription reaction system

| Reagent | Volume |
|---|---|
| Template RNA | 1 pg~1 μg |
| 4 × gDNA wiper Mix | 4 μL |
| RNase-free ddH$_2$O | Making up to 16 μL |

TABLE 7

Reverse transcription reaction procedure

| Temperature | Time |
|---|---|
| 50° C. | 15 min |
| 85° C. | 5 s |

(3) Detection of Cytokines by qRT-PCR

With spleen cDNA of mice in each group obtained in step (2) as a template, amplification primers for cytokines IL-4, IFN-γ, and TNF-α (Table 8) and a SYBR-Green-PCR kit were used to conduct qRT-PCR, and an expression level of a cytokine in the spleen of mice in each group relative to an internal reference gene GAPDH mRNA was detected by fluorescence quantification. With a GAPDH gene as an internal reference gene, the $2^{-\Delta\Delta Ct}$ method was used to compare the experimental group and the virulent S. suis attack control group. Due to the addition of a fluorophore to a PCR system, a change of a fluorescence signal was used to detect a change of an amount of each cyclic amplification product in the PCR amplification in real time, and a starting template was subjected to quantitative analysis through a Ct value and a standard curve.

According to Table 9, a qPCR system was prepared, and the fluorescence quantitative PCR amplification was conducted according to the following procedure: predenaturation at 95° C. for 30 s; 95° C. for 10 s and 60° C. for 30 s, with 40 cycles; and 95° C. for 15 s, 95° C. for 60 s, and 95° C. for 15 s. The cytokines IL-4, IFN-γ, and TNF-α and the GAPDH gene primers were synthesized by Nanjing GenScript Biotech Co., Ltd., as shown in Table 8.

TABLE 8

Cytokine primer sequences

| Target fragment | Primer sequence (from 5' end to 3' end) | Fragment size/bp | Annealing temperature (° C.) |
|---|---|---|---|
| GAPDH | P1: TGGCCTTCCGTGTTCCTAC (SEQ ID NO: 9)<br>P2: TGAAGTCGCAGGAGACAACC (SEQ ID NO: 10) | 1011 | 60 |
| TNF-α | P1: GAGTGACAAGCCTGTAGCCC (SEQ ID NO: 11)<br>P2: GACAAGGTACAACCCATCGG (SEQ ID NO: 12) | 1457 | 59 |
| IFN-γ | P1: AGCGGCTGACTGAACTCAGATTGTAG (SEQ ID NO: 13)<br>P2: GTCACAGTTTTCAGCTGTATAGGG (SEQ ID NO: 14) | 242 | 58 |

TABLE 8-continued

Cytokine primer sequences

| Target fragment | Primer sequence (from 5' end to 3' end) | Fragment size/bp | Annealing temperature (° C.) |
|---|---|---|---|
| IL-4 | P1: CGAAGAACACCACAGAGAGTGAGC (SEQ ID NO: 15) P2: GACTCATTCATGGTGCAGCTTATC (SEQ ID NO: 16) | 180 | 58 |

TABLE 9 qPCR system

| Reactant | Volume |
|---|---|
| 2 × ChamQ Universal SYBR Qrcr Master Mix | 10 μL |
| Forward primer | 0.4 μL |
| Reverse primer | 0.4 μL |
| cDNA | 2 μL |
| ddH$_2$O | Making up to 20 μL |

Figure 7:
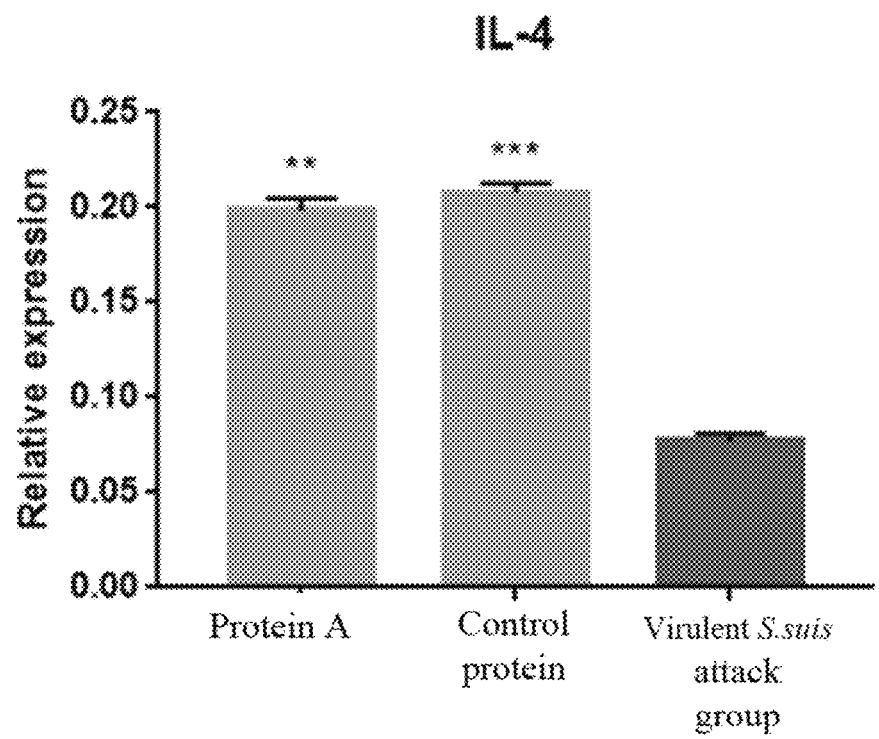
FIG. 7 shows the relative expression of IL-4 in spleens of mice in each group, where the protein A and the control protein refer to a protein A vaccine-immunized group and a control protein vaccine-immunized group, respectively, and the attack group refers to a virulent S. suis attack control group; and ** indicates P<0.01 compared with the virulent S. *suis* attack control group and *** indicates P<0.001 compared with the virulent *S. suis* attack control group.

As shown in FIG. 7, an expression level of IL-4 in the spleen of mice of the control protein vaccine-immunized group has an extremely significant difference (P<0.01) from that of the virulent S. suis attack control group, and an expression level of IL-4 in the spleen of mice of the protein A vaccine-immunized group has a significant difference (P<0.05) from that of the virulent S. suis attack control group.

Figure 8:
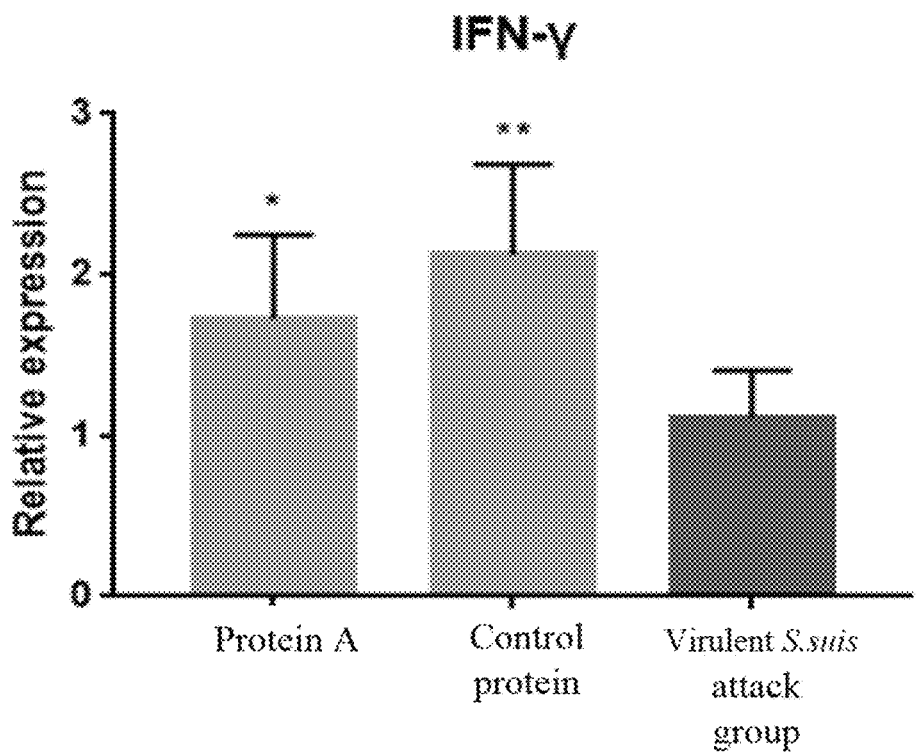
FIG. 8 shows the relative expression of IFN-γ in spleens of mice in each group, where the protein A and the control protein refer to a protein A vaccine-immunized group and a control protein vaccine-immunized group, respectively, and the attack group refers to a virulent *S. suis* attack control group; and * indicates P<0.05 compared with the virulent *S. suis* attack control group and ** indicates P<0.01 compared with the virulent *S. suis* attack control group.

As shown in FIG. 8, 14 days after the secondary immunization, a relative expression level of IFN-γ in the spleen of mice of each of the protein A vaccine-immunized group and the control protein vaccine-immunized group is significantly different from that of the virulent S. suis attack control group (P<0.05).

Figure 9:
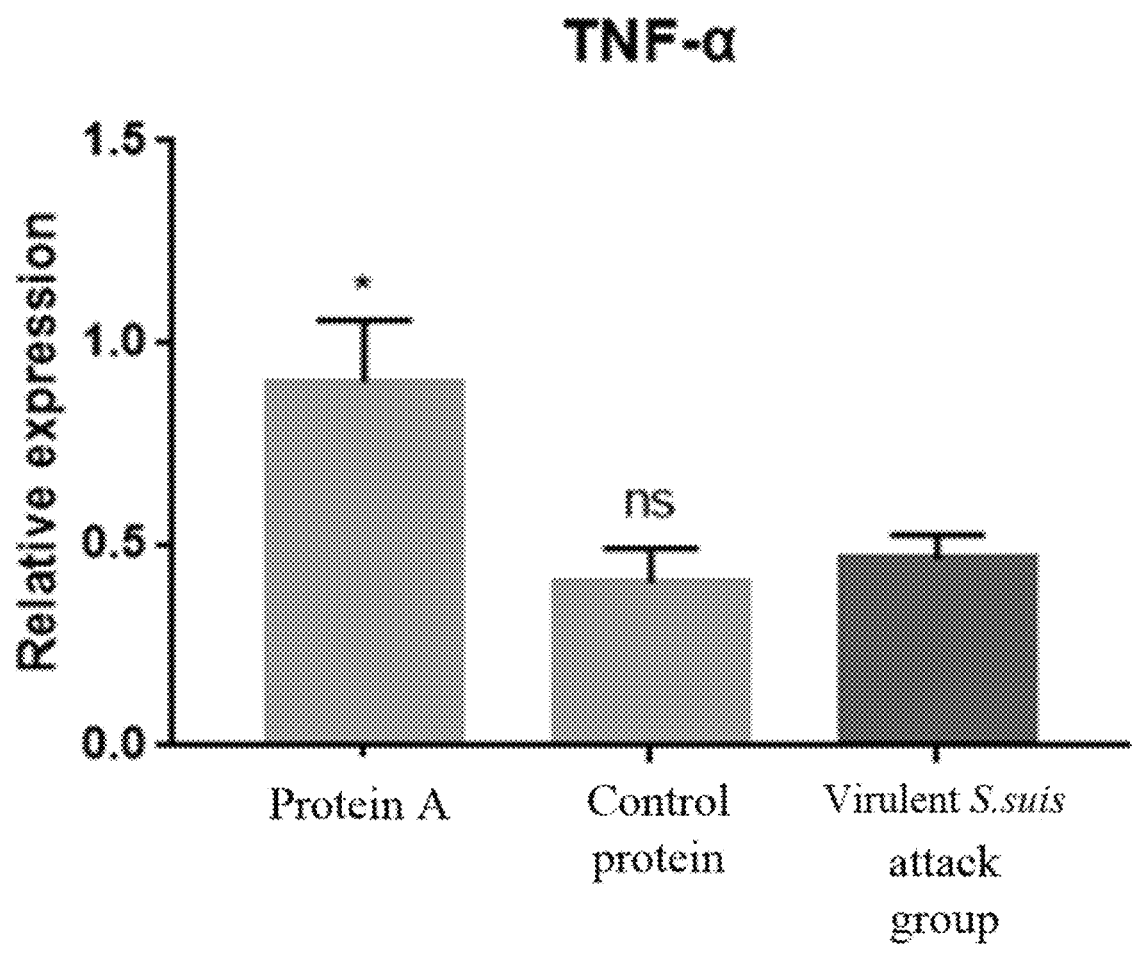

As shown in FIG. 9, 14 days after the secondary immunization, a relative expression level of INF-α in the spleen of mice of the protein A vaccine-immunized group is significantly different from that of the virulent S. suis attack control group (P<0.05), and a relative expression level of TNF-α in the spleen of mice of the control protein vaccine-immunized group is not significantly different from that of the virulent S. suis attack control group (P>0.05).

It can be seen from the above experiments that, after the mice immunized with the vaccines are attacked by S. suis serotype 2, 3, and 31, the protein A vaccine and the control protein vaccine can significantly increase a IgG antibody level in serum of mice; the protein A vaccine exhibits a protection rate of 100% against each of S. suis serotype 2, 3, and 31; and the control protein vaccine exhibits a protection rate of 100% only against S. suis serotype 2 and 31 and exhibits a protection rate only of 60% against S. suis serotype 3, that is, the control protein vaccine cannot effective resist the attack of S. suis serotype 3.

Protein A gene sequence (SEQ ID NO: 1)

ATGAGTTCAGGCAAAATTACTCAGGTTGTCGGACCAGTTGTAGACGTTGCGTTTG

CAGCAGAAGATAAACTTCCTGAGATTAACAACGCACTCGTTGTATATAAAAATGATGA

TTCCAAACAAAAAGTCGTGCTTGAAGTGGCTTTGGAACTTGGTGATGGCGTTGTACG

GACCATTGCCATGGAATCAACGGATGGATTGACACGTGGGATGGAAGTTCTCGATAC

AGGTCGTCCTATCTCAGTTCCAGTCGGTAAAGAAACCTTGGGTCGTGTCTTCAATGTG

TTGGGAGATACCATTGACCTTGAAGAGTCTTTTCCGGCAGATTTTGAACGTGAGCCTA

TCCATAAGAAAGCGCCAGCTTTTGACGAATTATCTACTTCAAGCGAAATTTTGGAAAC

AGGGATTAAGGTTATCGACCTCCTAGCACCTTATCTAAAAGGTGGTAAGGTTGGTCTC

TTCGGTGGTGCCGGTGTTGGTAAAACCGTTCTTATCCAAGAATTGATTCACAATATTG

CCCAAGAACACGGTGGTATCTCTGTGTTTACCGGAGTTGGCGAGCGTACCCGTGAAG

GGAACGATCTTTACTGGGAAATGAAAGAATCAGGTGTTATTGAAAAAACGGCCATGG

TATTTGGTCAGATGAATGAGCCACCAGGAGCCCGTATGCGGGTTGCTCTTACTGGTTT

GACCATTGCGGAATACTTCCGTGATGTGGAAGGGCAGGATGTTCTTCTGTTCATCGAC

AATATCTTCCGTTTCACTCAGGCTGGTTCAGAAGTGTCTGCCCTCTTGGGCCGTATGC

CATCAGCCGTTGGTTATCAGCCAACACTTGCAACTGAGATGGGACAATTGCAGGAGC

GTATTACCTCAACCAAGAAGGGTTCTGTTACATCTATTCAGGCTATTTACGTACCTGCA

GATGACTATACAGACCCAGCTCCAGCGACAGCTTTCGCTCACTTGGACTCGACTACC

AACTTGGAACGTAAGTTGACTCAGCTTGGTATCTACCCTGCGGTGGATCCGTTGGCGT

-continued

```
CATCATCTCGTGCGCTTTCTCCACAAATTGTTGGTGAAGAGCACTATACAGTGGCTAT

GGAAGTAAAACGTGTTCTTCAACGTTACCAAGAATTGCAAGATATTATTGCCATTCTC

GGTATGGATGAATTATCAGATGAAGAGAAGACCTTGGTTGGTCGCGCTCGTCGTATCC

AATTCTTCCTCTCTCAAAACTTCAACGTTGCGGAGCAATTTACAGGTATGCCAGGTTC

TTATGTGCCAGTAGCAGAAACGGTGAAAGGCTTTAAGGAAATCTTGGACGGCAAACA

CGACCATCTACCAGAAGATGCCTTCCGAAATGTTGGTTCAATTGAGGATGTGGTCGCT

AAAGCTGCTAAAATGAAATTCTAG
```

Protein A amino acid sequence:
(SEQ ID NO: 2)
```
MSSGKITQVVGPVVDVAFAAEDKLPEINNALVVYKNDDSKQKVVLEVALELGDGV

VRTIAMESTDGLTRGMEVLDTGRPISVPVGKETLGRVFNVLGDTIDLEESFPADFEREPIH

KKAPAFDELSTSSEILETGIKVIDLLAPYLKGGKVGLFGGAGVGKTVLIQELIHNIAQEHG

GISVFTGVGERTREGNDLYWEMKESGVIEKTAMVFGQMNEPPGARMRVALTGLTIAEYF

RDVEGQDVLLFIDNIFRFTQAGSEVSALLGRMPSAVGYQPTLATEMGQLQERITSTKKGS

VTSIQAIYVPADDYTDPAPATAFAHLDSTTNLERKLTQLGIYPAVDPLASSSRALAPQIVGE

EHYAVAMEVKRVLQRYQELQDIIAILGMDELSDEEKTLVGRARRIQFFLSQNFNVAEQFT

GMPGSYVPVAETVKGFKEILDGKHDHLPEDAFRNVGSIEDVVAKAAKMKF
```

Control protein gene sequence:
(SEQ ID NO: 3)
```
ATGACAAAATTAAATCGTGTAGTAGTAACAGGCTACGGTCTGACATCTCCAATCG

GAAATACGCCAGAGGAGTTCTGGAATAGTTTGAAGGCTGGGAAAATTGGGATCGGAA

AGATTACCAAGTTTGATACCAGTGAATATTCGGTCCATAATGCCGCGGAATTAAAAGA

TTTTCCTTTTGACAAATATTTCGTTAAAAAGGATACAAATCGCTACGATAATTACTCGC

TCTATGCACTCTATGCAGCTAAAGAAGCGATTGCTAATGCACAGCTGGATACAGAGAC

AGTGGATAGTGACCGTTTTGGCGTTATCTTATCAACAGGTATCGGTGGTATTTTGGAAA

TTGAAGAGCAAGTGGCTCGGATGAACGAAAAAGGTCCAAAACGCATTCGTCCCATG

GCTCTTCCAAAAGCTCTTCCAAATATGGCGGCCGGAAATATTGCCATGCAGGTCGGTG

CCAATGGTGTCTGCAAGTGTGTTATCACAGCCTGTGCTTCGTCAAATGATGCTTTAGG

GGAAGCCTTCCGTGAAATCAAGTTTGGTTTCCAAGATGTGATGCTGGCTGGCGGAGC

AGAGGCAGCCATTACTCCCTTTGCTATCGGTGGTTTCCAGGCTTTGACAGCTATGTCG

ACTACTGAGGATCCAGAACGTGCGTCTATTCCATTTGACAAGGACCGCAATGGTTTTG

TCATGGGAGAGGGTTCCGCGGTTTTAGTATTGGAAAGTTTGGAACACGCAGAGGCGC

GTGGAGCGACGATTTTGGCTGAAATCGTTGGTTATGGAAATACCTGCGATGCTTACCA

CATGACTTCTCCACATCCAGAAGGTCTGGGTGCTATTAAGGCCATGAAGTTGGCCATT

TCAGAAGCAGGTTTAGAGCCAGCTGATATTGATTACATCAATGCCCATGGCACTTCGA

CACCGGCTAATGAAAAGGGGAAAGCCAAGCTATCGTATCTGTCTTCGGCAAGAACA

CGCCAGTTTCTTCTACCAAGTCCTTCACTGGTCACTTGTTGGGTGCAGCGGGTGCCGT

TGAAGCGGCAGCTGTCATTGAGGCTATGCGTCATTCTTACGCACCAAAGACAGCTGG

TACGACAGAATTATCTGAAGATATTGAAGCGGATGTCATTTATGGACAGGGGCGTGAT

ATGGAAATCCGCCATGCCATTTCAAATACATTTGGCTTTGGTGGGCATAATTCAGTCAT

CGCTTTCAAACGTTGGGAGGCCTAA
```

Control protein amino acid sequence:
(SEQ ID NO: 4)

MTKLNRVVVTGYGLTSPIGNTPEEFWNSLKAGKIGIGKITKFDTSEYSVHNAAELKD

FPFDKYFVKKDTNRYDNYSLYALYAAKEAIANAQLDTETVDSDRFGVILSTGIGGILEIEE

QVARMNEKGPKRIRPMALPKALPNMAAGNIAMQVGANGVCKCVITACASSNDALGEA

FREIKFGFQDVMLAGGAEAAITPFAIGGFQALTAMSTTEDPERASIPFDKDRNGFVMGEG

SAVLVLESLEHAEARGATILAEIVGYGNTCDAYHMTSPHPEGLGAIKAMKLAISEAGLEP

ADIDYINAHGTSTPANEKGESQAIVSVFGKNTPVSSTKSFTGHLLGAAGAVEAAAVIEAM

RHSYAPKTAGTTELSEDIEADVIYGQGRDMEIRHAISNTFGFGGHNSVIAFKRWEA

What is claimed is:

1. A vaccine for *Streptococcus suis* (*S. suis*) comprising an isolated antigen and an effective amount of adjuvant, wherein lithe isolated antigen is a protein with the amino acid sequence shown in SEQ ID NO: 2, and the effective amount of adjuvant comprises a white oil.

2. A preparation method of the vaccine for *S. suis* according to claim 1, comprising the following steps: mixing white oil and aluminum stearate to obtain white oil adjuvant; adding polysorbate 80 to an aqueous solution of the protein with the amino acid sequence shown in SEQ ID NO: 2, and thoroughly mixing to obtain an isolated antigen solution; and mixing the isolated antigen solution with the white oil adjuvant according to a volume ratio of (0.5-1.5):2, and emulsifying to obtain the vaccine for *S. suis*.

3. The preparation method according to claim 2, wherein the protein is obtained by inserting a coding gene for the protein into a vector, introducing the vector into a host strain, and inducing expression.

4. The preparation method according to claim 3, wherein the coding gene for the protein has a sequence shown in SEQ ID NO: 1.

5. The preparation method according to claim 2, wherein a mass ratio of the white oil to the aluminum stearate is (90-120):2.5.

6. The preparation method according to claim 5, wherein the aqueous solution of the protein has a concentration of 0.9 mg/mL, to 1.2 mg/ml.

7. The preparation method according to claim 6, wherein a volume of the polysorhate 80 is 2% to 6% of a volume of the aqueous solution of the protein.

* * * * *

SEQUENCE LISTING

<160> NUMBER OF SEQ ID NOS: 16

<210> SEQ ID NO 1
<211> LENGTH: 1407
<212> TYPE: DNA
<213> ORGANISM: Streptococcus suis

<400> SEQUENCE: 1

```
atgagttcag gcaaaattac tcaggttgtc ggaccagttg tagacgttgc gtttgcagca      60
gaagataaac ttcctgagat taacaacgca ctcgttgtat ataaaaatga tgattccaaa     120
caaaaagtcg tgcttgaagt ggcttttgaa cttggtgatg cgttgtacg gaccattgcc      180
atggaatcaa cggatggatt gacacgtggg atggaagttc tcgatacagg tcgtcctatc     240
tcagttccag tcggtaaaga aaccttgggt cgtgtcttca atgtgttggg agataccatt     300
gaccttgaag agtctttttcc ggcagatttt gaacgtgagc ctatccataa gaaagcgcca     360
gcttttgacg aattatctac ttcaagcgaa atttttggaaa cagggattaa ggttatcgac     420
ctcctagcac cttatctaaa aggtggtaag gttggtctct cggtggtgc cggtgttggt      480
aaaaccgttc ttatccaaga attgattcac aatattgccc aagaacacgg tggtatctct     540
gtgtttaccg gagttggcga gcgtacccgt gaagggaacg atctttactg ggaaatgaaa     600
gaatcaggtg ttattgaaaa aacggccatg gtatttggtc agatgaatga gccaccagga     660
gcccgtatgc gggttgctct tactggtttg accattgcgg aatacttccg tgatgtggaa     720
gggcaggatg ttcttctgtt catcgacaat atcttccgtt tcactcaggc tggttcagaa     780
gtgtctgccc tcttgggccg tatgccatca gccgttggtt atcagccaac acttgcaact     840
gagatgggac aattgcagga gcgtattacc tcaaccaaga agggttctgt tacatctatt     900
caggctattt acgtacctgc agatgactat acagacccag ctccagcgac agctttcgct     960
cacttggact cgactaccaa cttggaacgt aagttgactc agcttggtat ctaccctgcg    1020
gtggatccgt tggcgtcatc atctcgtgcg ctttctccac aaattgttgg tgaagagcac    1080
tatacagtgg ctatggaagt aaaacgtgtt cttcaacgtt accaagaatt gcaagatatt    1140
attgccattc tcggtatgga tgaattatca gatgaagaga agaccttggt tggtcgcgct    1200
cgtcgtatcc aattcttcct ctctcaaaac ttcaacgttg cggagcaatt tacaggtatg    1260
ccaggttctt atgtgccagt agcagaaacg gtgaaaggct ttaaggaaat cttggacggc    1320
aaacacgacc atctaccaga agatgccttc cgaaatgttg gttcaattga ggatgtggtc    1380
gctaaagctg ctaaaatgaa attctag                                         1407
```

-continued

```
<210> SEQ ID NO 2
<211> LENGTH: 468
<212> TYPE: PRT
<213> ORGANISM: Streptococcus suis

<400> SEQUENCE: 2

Met Ser Ser Gly Lys Ile Thr Gln Val Val Gly Pro Val Val Asp Val
1               5                   10                  15

Ala Phe Ala Ala Glu Asp Lys Leu Pro Glu Ile Asn Asn Ala Leu Val
            20                  25                  30

Val Tyr Lys Asn Asp Asp Ser Lys Gln Lys Val Val Leu Glu Val Ala
        35                  40                  45

Leu Glu Leu Gly Asp Gly Val Val Arg Thr Ile Ala Met Glu Ser Thr
    50                  55                  60

Asp Gly Leu Thr Arg Gly Met Glu Val Leu Asp Thr Gly Arg Pro Ile
65                  70                  75                  80

Ser Val Pro Val Gly Lys Glu Thr Leu Gly Arg Val Phe Asn Val Leu
                85                  90                  95

Gly Asp Thr Ile Asp Leu Glu Glu Ser Phe Pro Ala Asp Phe Glu Arg
            100                 105                 110

Glu Pro Ile His Lys Lys Ala Pro Ala Phe Asp Glu Leu Ser Thr Ser
        115                 120                 125

Ser Glu Ile Leu Glu Thr Gly Ile Lys Val Ile Asp Leu Leu Ala Pro
    130                 135                 140

Tyr Leu Lys Gly Gly Lys Val Gly Leu Phe Gly Gly Ala Gly Val Gly
145                 150                 155                 160

Lys Thr Val Leu Ile Gln Glu Leu Ile His Asn Ile Ala Gln Glu His
                165                 170                 175

Gly Gly Ile Ser Val Phe Thr Gly Val Gly Glu Arg Thr Arg Glu Gly
            180                 185                 190

Asn Asp Leu Tyr Trp Glu Met Lys Glu Ser Gly Val Ile Glu Lys Thr
        195                 200                 205

Ala Met Val Phe Gly Gln Met Asn Glu Pro Pro Gly Ala Arg Met Arg
    210                 215                 220

Val Ala Leu Thr Gly Leu Thr Ile Ala Glu Tyr Phe Arg Asp Val Glu
225                 230                 235                 240

Gly Gln Asp Val Leu Leu Phe Ile Asp Asn Ile Phe Arg Phe Thr Gln
                245                 250                 255

Ala Gly Ser Glu Val Ser Ala Leu Leu Gly Arg Met Pro Ser Ala Val
            260                 265                 270

Gly Tyr Gln Pro Thr Leu Ala Thr Glu Met Gly Gln Leu Gln Glu Arg
        275                 280                 285

Ile Thr Ser Thr Lys Lys Gly Ser Val Thr Ser Ile Gln Ala Ile Tyr
    290                 295                 300

Val Pro Ala Asp Asp Tyr Thr Asp Pro Ala Pro Ala Thr Ala Phe Ala
305                 310                 315                 320

His Leu Asp Ser Thr Thr Asn Leu Glu Arg Lys Leu Thr Gln Leu Gly
                325                 330                 335

Ile Tyr Pro Ala Val Asp Pro Leu Ala Ser Ser Arg Ala Leu Ala
            340                 345                 350

Pro Gln Ile Val Gly Glu Glu His Tyr Ala Val Ala Met Glu Val Lys
        355                 360                 365

Arg Val Leu Gln Arg Tyr Gln Glu Leu Gln Asp Ile Ile Ala Ile Leu
    370                 375                 380
```

Gly Met Asp Glu Leu Ser Asp Glu Glu Lys Thr Leu Val Gly Arg Ala
385                 390                 395                 400

Arg Arg Ile Gln Phe Phe Leu Ser Gln Asn Phe Asn Val Ala Glu Gln
            405                 410                 415

Phe Thr Gly Met Pro Gly Ser Tyr Val Pro Val Ala Glu Thr Val Lys
            420                 425                 430

Gly Phe Lys Glu Ile Leu Asp Gly Lys His Asp His Leu Pro Glu Asp
            435                 440                 445

Ala Phe Arg Asn Val Gly Ser Ile Glu Asp Val Val Ala Lys Ala Ala
            450                 455                 460

Lys Met Lys Phe
465

<210> SEQ ID NO 3
<211> LENGTH: 1236
<212> TYPE: DNA
<213> ORGANISM: Streptococcus suis

<400> SEQUENCE: 3
atgacaaaat taaatcgtgt agtagtaaca ggctacggtc tgacatctcc aatcggaaat      60
acgccagagg agttctggaa tagtttgaag gctgggaaaa ttgggatcgg aaagattacc     120
aagtttgata ccagtgaata ttcggtccat aatgccgcgg aattaaaaga ttttcctttt     180
gacaaatatt tcgttaaaaa ggatacaaat cgctacgata attactcgct ctatgcactc     240
tatgcagcta aagaagcgat tgctaatgca cagctggata cagagacagt ggatagtgac     300
cgttttggcg ttatcttatc aacaggtatc ggtggtattt tggaaattga agagcaagtg     360
gctcggatga acgaaaaagg tccaaaacgc attcgtccca tggctcttcc aaaagctctt     420
ccaaatatgg cggccggaaa tattgccatg caggtcggtg ccaatggtgt ctgcaagtgt     480
gttatcacag cctgtgcttc gtcaaatgat gctttagggg aagccttccg tgaaatcaag     540
tttggttttc aagatgtgat gctggctggc ggagcagagg cagccattac tcccttttgct    600 atcggtggtt ccaggctttt gacagctatg tcgactactg aggatccaga acgtgcgtct     660
attccatttg acaaggaccg caatggtttt gtcatgggag agggttccgc ggttttagta     720
ttggaaagtt tggaacacgc agaggcgcgt ggagcgacga ttttggctga atcgttggt      780 tatgaaaata cctgcgatgc ttaccacatg acttctccac atccagaagg tctgggtgct     840
attaaggcca tgaagttggc catttcagaa gcaggtttag agccagctga tattgattac     900
atcaatgccc atggcacttc gacaccggct aatgaaaaag gggaaagcca agctatcgta     960
tctgtcttcg gcaagaacac gccagtttct tctaccaagt ccttcactgg tcacttgttg    1020
ggtgcagcgg gtgccgttga agcggcagct gtcattgagg ctatgcgtca ttcttacgca    1080
ccaaagacag ctggtacgac agaattatct gaagatattg aagcggatgt catttatgga    1140
caggggcgtg atatggaaat ccgccatgcc atttcaaata catttggctt tggtgggcat    1200
aattcagtca tcgctttcaa acgttgggag gcctaa                              1236

<210> SEQ ID NO 4
<211> LENGTH: 411
<212> TYPE: PRT
<213> ORGANISM: Streptococcus suis

<400> SEQUENCE: 4

Met Thr Lys Leu Asn Arg Val Val Val Thr Gly Tyr Gly Leu Thr Ser
1               5                   10                  15

Pro Ile Gly Asn Thr Pro Glu Glu Phe Trp Asn Ser Leu Lys Ala Gly
              20                  25                  30

Lys Ile Gly Ile Gly Lys Ile Thr Lys Phe Asp Thr Ser Glu Tyr Ser
         35                  40                  45

Val His Asn Ala Ala Glu Leu Lys Asp Phe Pro Phe Asp Lys Tyr Phe
 50                  55                  60

Val Lys Lys Asp Thr Asn Arg Tyr Asp Asn Tyr Ser Leu Tyr Ala Leu
 65                  70                  75                  80

Tyr Ala Ala Lys Glu Ala Ile Ala Asn Ala Gln Leu Asp Thr Glu Thr
                 85                  90                  95

Val Asp Ser Asp Arg Phe Gly Val Ile Leu Ser Thr Gly Ile Gly Gly
                100                 105                 110

Ile Leu Glu Ile Glu Glu Gln Val Ala Arg Met Asn Glu Lys Gly Pro
            115                 120                 125

Lys Arg Ile Arg Pro Met Ala Leu Pro Lys Ala Leu Pro Asn Met Ala
130                 135                 140

Ala Gly Asn Ile Ala Met Gln Val Gly Ala Asn Gly Val Cys Lys Cys
145                 150                 155                 160

Val Ile Thr Ala Cys Ala Ser Ser Asn Asp Ala Leu Gly Glu Ala Phe
                165                 170                 175

Arg Glu Ile Lys Phe Gly Phe Gln Asp Val Met Leu Ala Gly Gly Ala
            180                 185                 190

Glu Ala Ala Ile Thr Pro Phe Ala Ile Gly Gly Phe Gln Ala Leu Thr
            195                 200                 205

Ala Met Ser Thr Thr Glu Asp Pro Glu Arg Ala Ser Ile Pro Phe Asp
210                 215                 220

Lys Asp Arg Asn Gly Phe Val Met Gly Glu Gly Ser Ala Val Leu Val
225                 230                 235                 240

Leu Glu Ser Leu Glu His Ala Glu Ala Arg Gly Ala Thr Ile Leu Ala
                245                 250                 255

Glu Ile Val Gly Tyr Gly Asn Thr Cys Asp Ala Tyr His Met Thr Ser
            260                 265                 270

Pro His Pro Glu Gly Leu Gly Ala Ile Lys Ala Met Lys Leu Ala Ile
            275                 280                 285

Ser Glu Ala Gly Leu Glu Pro Ala Asp Ile Asp Tyr Ile Asn Ala His
290                 295                 300

Gly Thr Ser Thr Pro Ala Asn Glu Lys Gly Glu Ser Gln Ala Ile Val
305                 310                 315                 320

Ser Val Phe Gly Lys Asn Thr Pro Val Ser Ser Thr Lys Ser Phe Thr
                325                 330                 335

Gly His Leu Leu Gly Ala Ala Gly Ala Val Glu Ala Ala Ala Val Ile
            340                 345                 350

Glu Ala Met Arg His Ser Tyr Ala Pro Lys Thr Ala Gly Thr Thr Glu
            355                 360                 365

Leu Ser Glu Asp Ile Glu Ala Asp Val Ile Tyr Gly Gln Gly Arg Asp
370                 375                 380

Met Glu Ile Arg His Ala Ile Ser Asn Thr Phe Gly Phe Gly Gly His
385                 390                 395                 400

Asn Ser Val Ile Ala Phe Lys Arg Trp Glu Ala
                405                 410

<210> SEQ ID NO 5
<211> LENGTH: 33
<212> TYPE: DNA

```
<213> ORGANISM: Artificial Sequence
<220> FEATURE:
<223> OTHER INFORMATION: The sequence is synthetized.

<400> SEQUENCE: 5
ccgaattcat gagttcaggc aaaattactc agg                                    33

<210> SEQ ID NO 6
<211> LENGTH: 34
<212> TYPE: DNA
<213> ORGANISM: Artificial Sequence
<220> FEATURE:
<223> OTHER INFORMATION: The sequence is synthetized.

<400> SEQUENCE: 6
ccgctcgagg aatttcattt tagcagcttt agcg                                   34

<210> SEQ ID NO 7
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 7
ccgaattcat gacaaaatta aatcgtgtag tag                                    33

<210> SEQ ID NO 8
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 8
ccgctcgagg gcctcccaac gtttgaaagc g                                      31

<210> SEQ ID NO 9
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 9
tggccttccg tgttcctac                                                    19

<210> SEQ ID NO 10
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 10
tgaagtcgca ggagacaacc                                                   20

<210> SEQ ID NO 11
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 11
gagtgacaag cctgtagccc                                                   20
```

```
<210> SEQ ID NO 12
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 12
gacaaggtac aacccatcgg                                            20

<210> SEQ ID NO 13
<211> LENGTH: 26
<212> TYPE: DNA
<213> ORGANISM: Artificial Sequence
<220> FEATURE:
<223> OTHER INFORMATION: The sequence is synthetized.

<400> SEQUENCE: 13
agcggctgac tgaactcaga ttgtag                                     26

<210> SEQ ID NO 14
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 14
gtcacagttt tcagctgtat aggg                                       24

<210> SEQ ID NO 15
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 15
cgaagaacac cacagagagt gagc                                       24

<210> SEQ ID NO 16
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 16
gactcattca tggtgcagct tatc                                       24
```